(12) United States Patent
Kanehara et al.

(10) Patent No.: US 8,158,077 B2
(45) Date of Patent: Apr. 17, 2012

(54) COMPOSITION FOR DETECTION AND MODEL FOR EVALUATION OF FOOD PACKAGING MATERIAL USING THE SAME

(75) Inventors: Mie Kanehara, Kamisu (JP); Miki Yamasaki, Kurashiki (JP); Satoru Koike, Kurashiki (JP); Tomoyuki Watanabe, Kurashiki (JP)

(73) Assignee: Kuraray Co., Ltd., Kurashiki-shi (JP)

( * ) Notice: Subject to any disclaimer, the term of this patent is extended or adjusted under 35 U.S.C. 154(b) by 553 days.

(21) Appl. No.: 12/294,138

(22) PCT Filed: Mar. 22, 2007

(86) PCT No.: PCT/JP2007/056758
§ 371 (c)(1),
(2), (4) Date: Sep. 23, 2008

(87) PCT Pub. No.: WO2007/114202
PCT Pub. Date: Oct. 11, 2007

(65) Prior Publication Data
US 2009/0226576 A1    Sep. 10, 2009

(30) Foreign Application Priority Data

Mar. 29, 2006 (JP) .................. 2006-092520
Mar. 29, 2006 (JP) .................. 2006-092521

(51) Int. Cl.
*G01N 33/48* (2006.01)
(52) U.S. Cl. ........ 422/400; 422/420; 422/430; 436/127; 436/164; 436/166

(58) Field of Classification Search ............ 422/400, 422/420, 430; 436/127, 164, 166
See application file for complete search history.

(56) References Cited

U.S. PATENT DOCUMENTS

| 5,053,339 | A  | * | 10/1991 | Patel et al. ................. 436/2 |
| 6,254,831 | B1 | * | 7/2001 | Barnard et al. ............ 422/82.08 |
| 7,368,153 | B2 | * | 5/2008 | Barmore et al. ........... 428/36.71 |
| 2004/0115319 | A1 | | 6/2004 | Morris et al. |
| 2005/0037512 | A1 | | 2/2005 | Yeh et al. |
| 2006/0141106 | A1 | | 6/2006 | Kodama et al. |
| 2007/0111005 | A1 | | 5/2007 | Oshita et al. |

FOREIGN PATENT DOCUMENTS

| JP | 54-48294 | 4/1979 |
| JP | 58 210564 | 12/1983 |
| JP | 60-080763 | 5/1985 |
| JP | 61 152299 | 7/1986 |
| JP | 1 318957 | 12/1989 |
| JP | H1-318957 | * 12/1989 |
| JP | 6 281642 | 10/1994 |
| JP | 08-118551 | 5/1996 |
| JP | 10-030986 | 2/1998 |
| JP | 11-174039 | 7/1999 |
| JP | 2002 257813 | 9/2002 |

(Continued)

*Primary Examiner* — Lyle Alexander
(74) *Attorney, Agent, or Firm* — Oblon, Spivak, McClelland, Maier & Neustadt, L.L.P.

(57) ABSTRACT

The present invention provides a composition for detecting an object substance (X). This detection composition contains a gel (Y). The gel (Y) contains a colorable aqueous solution (A) that can be colored upon contact with the object substance (X), and a crosslinked polymer (B). This composition is preferably used to evaluate packaging materials.

20 Claims, 2 Drawing Sheets

FOREIGN PATENT DOCUMENTS

| | | |
|---|---|---|
| JP | 2003-064317 | 3/2003 |
| JP | 2005-091008 | 4/2005 |
| WO | 98/15645 * | 4/1998 |
| WO | WO 03/036270 A1 | 5/2003 |
| WO | 2005-052572 | 6/2005 |
| WO | 2005-053954 | 6/2005 |
| WO | WO 2006/030283 A1 | 3/2006 |

* cited by examiner

COMPOSITION FOR DETECTION AND MODEL FOR EVALUATION OF FOOD PACKAGING MATERIAL USING THE SAME

TECHNICAL FIELD

The present invention relates to a detection composition and a food packaging material evaluation model (sample for evaluating food packaging materials). More specifically, the present invention relates to a composition for detecting an object substance (X), containing a gel (Y) that contains a colorable aqueous solution (A) colored upon contact with the object substance (X) and a crosslinked polymer (B), and a food packaging material evaluation model using the same. Furthermore, the present invention relates to a method for detecting penetration of an object substance (X) into a packed body, using the above-mentioned detection composition, and a method for evaluating a packaging material, using the detection composition.

BACKGROUND ART

In a case where food is packed with a packaging material and stored, food deterioration is often accelerated by a substance penetrating from the exterior of the packed body. In order to prevent food from being deteriorated by a substance penetrated from the exterior, methods are conventionally adopted in which food is packed with a packaging material having low substance permeability, in particular, gas permeability. Typical examples of such substance that penetrates from the exterior and accelerates food deterioration include oxygen. In this case, methods are adopted, for example, in which food is packed with a packaging material having low oxygen permeability, and moreover, an oxygen absorbent is enclosed within the packaging container or the like.

In a case where methods are adopted in which a substance is prevented from penetrating from the exterior into food or in which the substance is absorbed, a means for detecting the substance that has penetrated from the exterior and judging the influence of the substance on the food is necessary in order to determine the effectiveness of these methods. Mechanical measurement methods are accurate, but more simply, methods using a color reaction of indicators are used. Various detection methods have been conventionally proposed in particular for oxygen.

For example, Japanese Laid-Open Patent Publication No. 54-48294 discloses an oxygen detecting composition comprising methylene blue and a reducing agent in an amount that can change the methylene blue to substantially colorless in the presence of water, wherein the oxygen detecting composition is colored upon detection of oxygen. Japanese Laid-Open Patent Publication No. 8-118551 discloses a composition consisting of methylene blue, hydrosulfite ($Na_2S_2O_4$), agar, and water, and a method for detecting oxygen penetrated into a container using the composition. Japanese Laid-Open Patent Publication No. 2005-91008 discloses an oxygen indicator in which a redox indicator is contained in various supports.

Penetration of oxygen is detected, for example, by enclosing such oxygen detection means within the interior of a packed body of various types of food, when selling the food. However, for example, assuming that food such as meat or ham having a certain size and shape is packed, most of such means in these states are often insufficient for checking the barrier property of the packaging material per se, or the barrier property of a bag or container made of the packaging material, under suitable conditions for handling the food.

For example, in a method for checking penetration of oxygen based on a color change of methylene blue by placing an aqueous solution containing methylene blue and a reducing agent in a packaging material in a predetermined form such as a container or bag, it is possible to judge whether or not as a whole, oxygen has penetrated, but it is impossible to judge from which portion of the container or bag, the oxygen has penetrated. The reason for this is that the aqueous solution flows and convectively circulates in the interior of the container or bag. In particular, in a case where the shape of the packaging material is changed according to the shape of the food, or in a case where the packaging material is subjected to external treatment such as heat treatment depending on the treatment conditions for food, it is difficult to judge the barrier property or the like of the packaging material.

As disclosed in Japanese Laid-Open Patent Publication No. 54-48294, it is possible to prevent an aqueous solution containing methylene blue and a reducing agent from flowing or convectively circulating, by impregnating a support such as paper or film with the aqueous solution, or by printing the aqueous solution onto paper. However, in both of these prevention methods, since the detection means are realized in the form of a film, it is impossible to test the barrier property of packaging materials under conditions that match various forms of food or various types of treatment necessary for food. For example, even though it is possible to detect oxygen penetrating into the packed body, it is impossible to detect whether the oxygen has penetrated through the entire packaging material or the oxygen has penetrated through a pinhole that has been present in the packaging material.

DISCLOSURE OF INVENTION

The inventors of the present invention have investigated detection compositions that may be used for the above-described food packaging material evaluation model. Assuming food models made of materials that have a predetermined shape of food and enables a predetermined substance such as oxygen to be detected, and assuming food packaging material evaluation models in which the food models are packed, the inventors have investigated detection compositions that can be used for these models.

First, research was conducted on a material as in Japanese Laid-Open Patent Publication No. 54-48294, in which paper was used as a support and impregnated with a detection solution containing methylene blue and a reducing agent. This material is inappropriate as the detection composition because it is in the form of a film and is opaque. For example, with this material, it is difficult to determine the level of depth to which the penetrated oxygen has reached, in the interior of the food packaging material evaluation model.

Japanese Laid-Open Patent Publication No. 54-48294 discloses a polyhydroxyethyl methacrylate film as a support. In a case where it is attempted to form a food packaging material evaluation model using this film, it is difficult to sufficiently impregnate the film with a detection solution.

In the case of the composition disclosed in Japanese Laid-Open Patent Publication No. 8-118551, comprising agar, methylene blue, water, and the like, oxygen penetration can be detected without any problem, by placing the composition in a cup or the like that can retain a predetermined shape. However, in a case where it is attempted to use this composition as a food model packed with a flexible packaging material, it is difficult to retain the shape. Thus, this composition is not suitable for using as a food model that is packed in a state where the outer surface thereof is brought into close contact with a flexible packaging material. Furthermore, even if the composition can be retained in a predetermined shape, the composition liquifies and flows when subjected to heat treatment. Thus, this composition is not suitable for testing the property of a packaging material, for example, when exposed to conditions such as heat sterilization.

Japanese Laid-Open Patent Publication No. 2005-91008 also discloses various detection compositions as examples. However, there are problems similar to those described above because any compositions are either those in which an opaque and film-like material is impregnated with a detection solution or those in which a gel without sufficient hardness and thermal resistance contains a detection solution.

The present invention was made in order to solve the above-described conventional problems.

A detection composition of the present invention is a composition for detecting an object substance (X), wherein the composition contains a gel (Y), and the gel (Y) contains a colorable aqueous solution (A) that can be colored upon contact with the object substance (X), and a crosslinked polymer (B).

In a certain embodiment, the crosslinked polymer (B) is constituted by a water-absorbent crosslinked polymer, and the colorable aqueous solution (A) is retained in the water-absorbent crosslinked polymer to form the gel (Y).

In a certain embodiment, the gel (Y) is obtained in a step comprising crosslinking a mixture that contains the colorable aqueous solution (A) and a crosslinkable polymer.

In a certain embodiment, the gel (Y) is in the form of particles.

In a certain embodiment, the gel (Y) is particles having a particle size of 0.01 to 10 mm.

In a certain embodiment, the gel (Y) is in the form of blocks.

In a certain embodiment, when the gel (Y) is heated at 85° C. for 15 minutes in the presence of an excessive amount of water, the shape of the gel (Y) can be retained.

In a certain embodiment, the crosslinked polymer (B) is at least one selected from the group consisting of a crosslinked product of a maleic anhydride-isobutene copolymer, its salt, and crosslinked PVA.

In a certain embodiment, the colorable aqueous solution (A) is an aqueous solution that contains a color reagent (A1) colored upon contact with the object substance (X), and an adjustment substance (A2), and the adjustment substance (A2) can keep the color reagent (A1) colorless until contact with the object substance (X).

In a certain embodiment, the object substance (X) is oxygen.

In a certain embodiment, the color reagent (A1) is methylene blue.

In a certain embodiment, the adjustment substance (A2) is stannous chloride, and the composition further contains a hydrochloric acid.

In a certain embodiment, the composition further contains a humidity control substance (C) for adjusting equilibrium vapor pressure.

A food model of the present invention is obtained by shaping the detection composition.

A food packaging material evaluation model of the present invention is obtained by sealing and packing the detection composition using a packaging material.

A food packaging material evaluation model of the present invention is obtained by performing inert gas replacement on the detection composition, placing the detection composition in a packaging material in the form of a container or bag, and then sealing the packaging material.

A food packaging material evaluation model of the present invention is obtained by placing the detection composition in a packaging material in the form of a container or bag, discharging a gas, and then sealing the detection composition with the packaging material.

A food packaging material evaluation model of the present invention is obtained by placing the detection composition in a packaging material in the form of a container or bag, sealing the detection composition with the packaging material, and then performing ultraviolet sterilization or heat sterilization.

A method for detecting penetration of an object substance (X) into a packed body, of the present invention comprises: sealing and packing the detection composition using a packaging material; bringing an obtained packed body into contact with a gas or liquid that contains the object substance (X); and detecting the object substance (X) based on coloring of the composition in the interior of the packed body, thereby detecting penetration of the object substance (X) into the packed body.

A method for evaluating a packaging material of the present invention comprises: sealing and packing the detection composition using the packaging material; bringing an obtained packed body into contact with a gas or liquid that contains an object substance (X); and detecting the object substance (X) that has penetrated into the packed body based on coloring of the detection composition in the interior of the packed body, thereby evaluating the packaging material.

In a certain embodiment, the packaging material to be evaluated is a food packaging material.

Accordingly, the present invention can achieve the following aims: to provide a detection composition that can form a food packaging material evaluation model, capable of easily detecting whether or not there is penetration of a predetermined object substance such as oxygen, into a packed body in a case where food having a predetermined shape and property, in particular, food having a certain thickness and predetermined shape is packed; to provide a food packaging material evaluation model using the composition; to provide a food packaging material evaluation model that enables penetration of the object substance to be easily detected even in a case where treatment (e.g., heat treatment for the purpose of sterilization or the like) necessary for the food packed body is performed; to provide a method for detecting penetration of the object substance into the packed body, using the detection composition; and to provide a method for evaluating a packaging material, using the detection composition.

Figure 1:
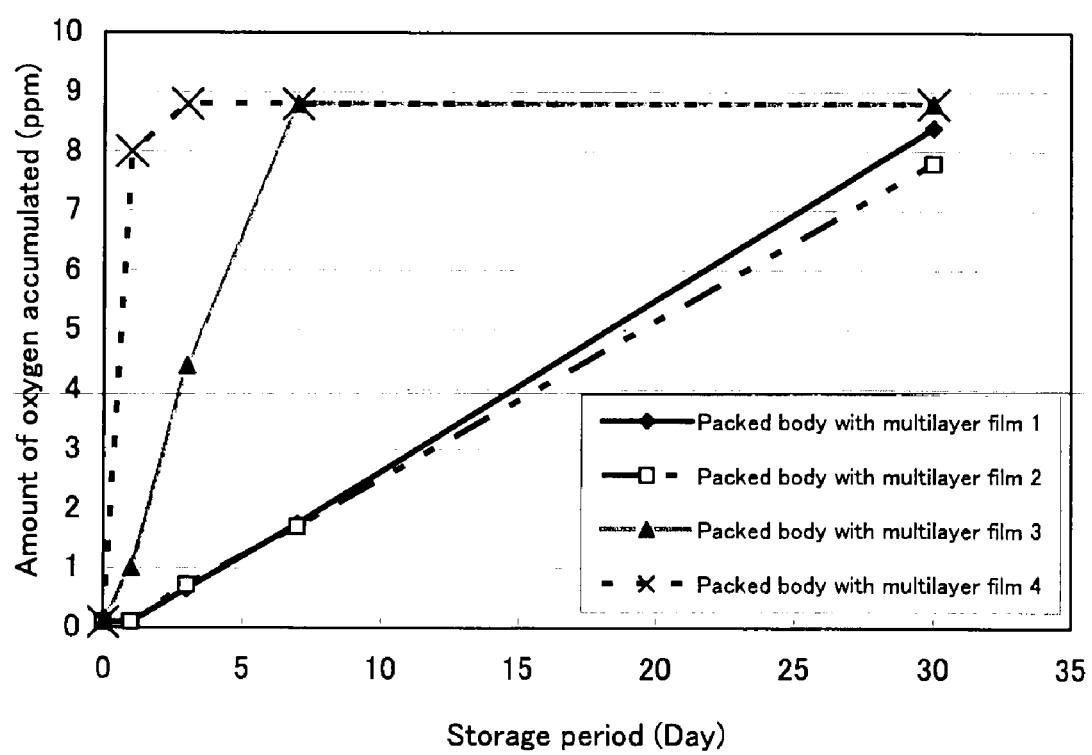
FIG. 1 is a graph showing the relationship between the storage time and the amount of oxygen penetrated, in food packaging material evaluation models of the present invention.

Best Mode for Carrying Out the Invention

A composition for detecting an object substance (X) of the present invention contains a gel (Y). The gel (Y) contains a colorable aqueous solution (A) that can be colored upon contact with the object substance (X), and a crosslinked polymer (B). Hereinafter, these materials, food packaging material evaluation models using the composition, methods for detecting penetration of the object substance (X) into the packed body, and methods for evaluating packaging materials will be sequentially described.

(1) The Object Substance (X) and the Colorable Aqueous Solution (A)

The object substance (X) that can be detected by the detection composition of the present invention is a substance that is to be detected, typically, a substance that may deteriorate food. Representative examples of the substance include oxygen and carbon dioxide. Examples thereof further include acidic gases such as hydrogen chloride gas, and basic gases such as ammonia gas. In particular, oxygen is a representative substance that may deteriorate food.

As the colorable aqueous solution (A), typically, an aqueous solution is used that has the property of being completely transparent or substantially transparent until contact with the object substance (X) and being colored upon contact with the object substance (X). Regarding the transparency of the colorable aqueous solution (A), when the food model has a certain thickness and is obtained by preparing a gel (Y) that contains the colorable aqueous solution (A) and a crosslinked polymer (B) described later, the food model may be transparent to the extent that a food model can be seen through the solution in the thickness direction. Typically, such a colorable aqueous solution (A) is an aqueous solution that contains a color reagent (A1) colored upon contact with the object substance (X), and optionally an adjustment substance (A2) and the like. The adjustment substance (A2) is a compound that can keep the color reagent (A1) colorless until contact with the object substance (X).

Alternatively, the colorable aqueous solution (A) may have a predetermined color from the beginning, and the color hue or the shade of the color may change upon contact with the object substance (X), and the change may be clearly observed.

In a case where the object substance (X) is oxygen, a redox indicator is used as a representative example of the color reagent (A1). Examples of the redox indicator include methylene blue, methyl red, anthocyanin, anthraquinone, β-carotene, methyl orange, litmus, bromothymol blue, and phenolphthalein. Methylene blue is preferably used, for example, in view of clearity of coloration. In this case, a reducing agent is used as the adjustment substance (A2). Examples of the reducing agent include stannous salts such as stannous chloride ($SnCl_2$), hydrosulfite salts ($S_2O_3^{2-}$), and ascorbic acids. In a case where stannous chloride is used as the reducing agent, a hydrochloric acid may be used in combination.

In a case where the object substance (X) is carbon dioxide, bromothymol blue (BTB indicator) or metacresol purple is used as the color reagent (A1). In a case where the object substance (X) is ammonia, Nessler's reagent is used as the color reagent (A1). In a case where the object substance (X) is an acidic or basic gas or the like, an indicator that is colored upon a change in pH, such as bromothymol blue (BTB indicator), methyl orange, litmus, and phenolphthalein, is used as the color reagent (A1), and a pH adjuster such as a basic or acidic aqueous solution is used as the adjustment substance (A2).

There is no specific limitation on the amounts of the color reagent (A1) and the adjustment substance (A2) contained, and they are determined as appropriate depending on the type of the object substance (X), the application form of an obtained food packaging material evaluation model, and the like. For example, in a case where the object substance (X) is oxygen, if a redox indicator and a reducing agent are contained as the color reagent (A1) and the adjustment substance (A2) respectively, and the composition is used as a large food packaging material evaluation model under strict inert gas replacement, the amount of the reducing agent may be around the minimum amount necessary for converting the redox indicator into the reduced form. In a case where the amount used is small, and materials of the detection composition are placed in a packaging container or bag in air, the reducing agent may be used in an excessive amount according to the operation status.

The specific amount of the color reagent (A1) is selected as appropriate, for example, depending on the penetration amount of the object substance (X) to be penetrating. Typically, the color reagent (A1) is contained in an amount of about 1 mg to 10 g, preferably about 10 mg to 1 g, with respect to 1 kg of the colorable aqueous solution (A). In a case where the object substance (X) is oxygen, and the redox indicator and the reducing agent are used, the reducing agent is contained at least in an amount in which the redox indicator can be changed to be substantially colorless, but also may be used in an excessive amount as appropriate according to the handling conditions. For example, in a case where the detection composition has to be handled in air before being placed in a packaging container or bag, it is practically effective that the reducing agent is used in an excessive amount in order to prevent coloring from starting during placing the detection composition. The reducing agent is used, for example, in an amount of about 0.1 to 10 mol with respect to 1 mol of the redox indicator.

(2) The Crosslinked Polymer (B)

The crosslinked polymer (B) used in the present invention has a function as a matrix polymer that forms the gel (Y), in the detection composition of the present invention. The crosslinked polymer (B) is a hydrophilic polymer having a crosslinked structure.

Preferable types of the crosslinked polymer (B) vary depending on the form of the gel (Y) in the composition as described below.

There are mainly two following types of the gel (Y) that is contained in the composition of the present invention. A first gel is obtained by the following method (hereinafter, this method may be referred to as a first method). A water-absorbent crosslinked polymer is prepared in advance. The polymer is caused to absorb the colorable aqueous solution (A), and optionally a humidity control substance (C) and additives described later, for example. Thus, a gel constituted by the crosslinked polymer (B) that retains (is impregnated with) the colorable aqueous solution (A) is formed (hereinafter, in this specification, this first gel may be referred to as a gel (Y1)). A second gel is obtained by the following method (hereinafter, this method may be referred to as a second method). A mixture is prepared that contains a polymer (crosslinkable polymer) capable of forming the crosslinked polymer (B), the colorable aqueous solution (A), and optionally the humidity control substance (C) and additives described later, for example. This mixture is subjected to crosslinking treatment, and thus a gel (hereinafter, in this specification, this second gel may be referred to as a gel (Y2)) is formed. In this gel (Y2), the constituents (the color reagent (A1), etc.) in the colorable aqueous solution (A) are retained in the matrix of the crosslinked polymer (B).

There is no specific limitation on the water-absorbent crosslinked polymer used for forming the first gel (Y1), as long as it is a water-absorbent polymer having a crosslinked structure. It is preferable that the water-absorbent crosslinked polymer per se is transparent, or becomes substantially transparent when absorbing the aqueous solution. As such a polymer, either a natural product-derived polymer or a synthetic polymer can be used. Examples of the natural product-derived polymer include crosslinked polymers obtained by crosslinking naturally-occurring polymers such as a polyglutamic acid-based polymer, a starch-based polymer, a carrageenan-based polymer, or a chitin-based polymer. Examples of the synthetic polymer include crosslinked products of hydrophilic polymers, such as crosslinked products of a polyvinyl alcohol-based polymer, crosslinked products of an unsaturated carboxylic acid-based polymer, and alkali metal salts thereof.

Among these crosslinkable polymers (base polymers) that can form crosslinked polymers, examples of the polyvinyl alcohol-based polymer include polyvinyl alcohol (hereinafter PVA) and an ethylene-vinyl alcohol copolymer. Examples of the unsaturated carboxylic acid-based polymer include a homopolymer of a (meth)acrylic acid or its derivative, a copolymer including (meth)acrylic acid and styrene or a diene compound (e.g., styrene-(meth)acrylic acid copolymer), a homopolymer of a maleic anhydride derivative, a copolymer including maleic anhydride and an olefin or a diene compound (e.g., maleic anhydride-isobutene copolymer).

As the water-absorbent crosslinked polymer, chemically crosslinked hydrophilic synthetic polymers are preferable, for example, in view of stability during storage and ease of adjustment of degree of crosslinking. For example, water-absorbent crosslinked polymers are preferably used, such as a crosslinked maleic anhydride-isobutene copolymer and a crosslinked (meth)acrylic acid-based polymer. Herein, "(meth)acrylic acid" refers to at least one of an acrylic acid and a methacrylic acid.

In a case where a water-absorbent crosslinked polymer is used, if the water absorbability is too low, it may be difficult to obtain detectivity close to that of food. Thus, a crosslinked polymer is used that can absorb water in a weight of preferably 1 time or more, more preferably 10 times or more its own weight. For example, in a case where a detection composition for detecting oxygen is to be formed, a crosslinked polymer is preferable that can absorb water in a weight of about 50 times or more its own weight, in view of diffusibility of the oxygen. Conversely, if the water absorbability is too high, the polymer gel may not keep sufficient hardness. Thus, polymer particles are used that absorb water in a weight of preferably 1000 times or less, more preferably 500 times or less its own weight.

As the crosslinkable polymer used for preparing the second gel (Y2), polymers (polymers before crosslinking treatment) can be used that are capable of forming the water-absorbent crosslinked polymers used for the first gel (Y1). In particular, polyvinyl alcohol-based polymers are preferable, such as polyvinyl alcohol (hereinafter, may be referred to as PVA) and ethylene-vinyl alcohol copolymer. The crosslinking treatment is performed typically using a crosslinking agent. A crosslinking reaction progresses by adding a crosslinking agent or the like to a mixture containing the above-described crosslinkable polymer, the colorable aqueous solution (A), and optionally the humidity control substance (C) and additives described later, for example. As the crosslinking agent, boric acid compounds, titanium compounds (titanium lactate, etc.), dialdehyde compounds (glutaraldehyde, etc.), or the like can be used.

In both the gel (Y1) and the gel (Y2), it is possible to adjust the hardness of the gel by adjusting factors such as the type of the crosslinked polymer (B) finally contained in the gel, the degree of crosslinking, or the ratio in amount between the crosslinked polymer (B) and the colorable aqueous solution (A) appropriately. The hardness of the gel (Y) is adjusted as appropriate according to the hardness of food that is assumed as a content of the packed body.

In the case of the first gel (Y1), a polymer having a desired degree of crosslinking is selectively used. In the case of the second gel (Y2), the degree of crosslinking is adjusted as appropriate by adjusting the type of a crosslinkable polymer, the type of a crosslinking agent, their amounts, reaction time, or the like, when preparing the second gel (Y2). There is no specific limitation on the degree of crosslinking in these cases, and it is determined as appropriate according to the purpose. Typically, the degree of crosslinking is preferably about 0.5 to 20, or about 1.0 to 15. If the degree of crosslinking is too high, the formed gel per se has a barrier property. In this case, diffusion of the object substance (X) to the interior is inhibited, and thus it may be difficult for the object substance (X) to penetrate into the packed body. If the degree of crosslinking is too low, appropriate hardness or hot water resistance may not be obtained.

Furthermore, regardless whether the gel (Y) is the gel (Y1) or the gel (Y2), it is preferable that the gel does not become fluid even in heat treatment, for example, in order to check the barrier property or the like of the packaging material when exposed to sterilization conditions. That is to say, it is preferable that, in a case where the crosslinked polymer (B) is heated in the coexistence with an excessive amount of water, the shape of the gel can be retained. More specifically, the gel preferably does not change its shape to fluid, when heated in the presence of water in an amount of 100 parts by weight or more, more preferably 500 parts by weight or more, and particularly preferably 5000 parts by weight or more, with respect to 100 parts by weight of the crosslinked polymer. Here, in the case of the gel (Y1), the weight of the crosslinked polymer refers to the weight of the water-absorbent crosslinked polymer. In the case of the gel (Y2), it refers to the weight of the crosslinked polymer that is contained in the gel (Y2) formed by crosslinking treatment, and is calculated typically based on the weight of the crosslinkable polymer as the raw materials. The heating condition of the gel (Y) is such that the gel is heated at 85° C. for 15 minutes or more assuming typical hot water sterilization, at 100° C. for 15 minutes or more assuming boiling conditions, and at 120° C. for 30 minutes or more assuming retort sterilization. It is preferable that the gel does not become fluid when treated under this condition.

(3) The Humidity Control Substance (C) and Additives

The humidity control substance (C) that is optionally contained in the detection composition of the present invention functions as a water vapor pressure adjuster, and is contained in the composition in a range where not impairing the effect of the detection composition per se. More specifically, adding such a humidity control substance (C) makes it possible to adjust the water vapor pressure of the detection composition in equilibrium state according to the type and amount (concentration) of the humidity control substance (C). For example, in a case where the barrier property of a barrier packaging material is affected by humidity, the humidity control substance (C) makes it possible to reproduce the conditions of the water vapor pressure assumed in a case where predetermined food containing water is packed, for example, in order to perform a test of the packaging material.

Examples of the compound that can be such a water vapor pressure adjuster include: alkali metal salts (sodium hydroxide, sodium chloride, sodium bromide, sodium acetate, sodium sulfate, sodium nitrate, potassium hydroxide, potassium chloride, potassium bromide, potassium acetate, potassium sulfate, potassium nitrate, etc.); alkaline earth metal salts (calcium salts, magnesium salts, etc. of compounds similar to the above, such as calcium hydroxide or magnesium chloride); ammonium salts (ammonium salts of compounds similar to the above, such as ammonium hydroxide, ammonium chloride, or ammonium bromide); urea; and sugars such as sucrose and glucose.

Examples of the additives that can be contained in the detection composition of the present invention include: antiseptics and alcohol for suppressing propagation of microorganisms when constituents of the composition are mixed and stored; stabilizers for preventing the composition from being deteriorated by light; and other various food additives that are added to food. These additives are contained in a range where not impairing the effect of the detection composition per se.

(4) The Detection Composition Containing the Gel (Y) that Contains the Colorable Aqueous Solution (A) and the Crosslinked Polymer (B), and the Food Packaging Material Evaluation Model Using the Same The composition for detecting the object substance (X) of the present invention contains the gel (Y) that contains the colorable aqueous solution (A), the crosslinked polymer (B), and optionally the humidity control substance (C) and additives described above, for example. There is no specific limitation on the form of the gel (Y), but it is typically particles or blocks (lumps). The composition that contains the particle or block gel (Y) is formed into a food packaging material evaluation model, by packing the composition with a predetermined packaging material as described later.

Hereinafter, the particle gel (Y) may be referred to as a gel (Yp), and the block gel (Y) may be referred to as (Yb). Furthermore, the particle gel (Yp) constituted by the gel (Y1) may be referred to as a particle gel (Y1p) or a gel (Y1p). The block gel (Yb) constituted by the gel (Y1) may be referred to as a block gel (Y1b) or a gel (Y1b). The particle gel (Yp) constituted by the gel (Y2) may be referred to as a particle gel (Y2p) or a gel (Y2p). The block gel (Yb) constituted by the gel (Y2) may be referred to as a block gel (Y2b) or a gel (Y2b).

(4.1) The Detection Composition and the Food Packaging Material Evaluation Model, Containing the Particle Gel As described above, the particle gel (Yp) may be the particle gel (Y1p) constituted by the gel (Y1), or the particle gel (Y2p) constituted by the gel (Y2).

The particle gel (Y1p) is formed by a method (the above-described first method) in which the colorable aqueous solution (A), and optionally the humidity control substance (C) and additives described above are added to the water-absorbent crosslinked polymer particles or powder described above. The particle gel (Y2p) is formed by a method (method based on the above-described second method) in which an uncrosslinked gel that contains the crosslinkable polymer, the colorable aqueous solution (A), and optionally the humidity control substance (C) and additives is prepared, formed into particles, and then crosslinked using a crosslinking agent or the like. Alternatively, an uncrosslinked block gel may be prepared, crosslinked, and then cut into particles having an appropriate size.

In the first method for preparing the gel (Y1p), it is preferable that the colorable aqueous solution (A) is mixed in an amount of 100 parts by weight or more, preferably 300 parts by weight or more, and more preferably 500 parts by weight or more, with respect to 100 parts by weight of the crosslinked polymer. However, if the amount of the colorable aqueous solution is too large, it exceeds the amount of the colorable aqueous solution that can be absorbed by the crosslinked polymer, and thus the colorable aqueous solution that cannot be carried by the polymer may remain in the gel. Even in such a state, the composition per se can be used, but the amount of the colorable aqueous solution (A) is typically 20000 parts by weight or less, preferably 10000 parts by weight or less, more preferably 7000 parts by weight or less, and particularly preferably 5000 parts by weight or less, with respect to 100 parts by weight of the crosslinked polymer. With this method, the particle gel (Y1p) is formed in which the colorable aqueous solution (A), and optionally the humidity control substance (C) and additives described above are absorbed by the crosslinked polymer (B).

This first method is preferable because it can be simply and easily performed. As the water-absorbent crosslinked polymer, for example, the above-mentioned crosslinked products of a poly(meth)acrylic acid and their salts, and crosslinked products of a maleic anhydride-isobutene copolymer and their salts are particularly preferable.

There is no specific limitation on the particle size of the particle gel (Yp), and it is selected as appropriate, for example, according to the size of assumed food. If the particle size is too small, diffusion between the particles may not take place freely, which reduces the detection speed. Conversely, if the particle size is too large, it becomes difficult to retain the shape as a food model. From these points of view, the particle size is preferably 0.01 mm or more, more preferably 0.02 mm or more, and even more preferably 0.1 mm or more. Moreover, the particle size is preferably 10 mm or less, more preferably 7 mm or less, and even more preferably 5 mm or less. The particle size of the gel (Yp) is preferably 0.01 to 1 mm because with this particle size, the gel particles can be easily handled, and air is less mixed between the particles when enclosed within a packaging material or the like. Alternatively, the particle size is preferably 2 to 7 mm because with this particle size, the shape of a food packaging material evaluation model can be easily retained when the particles are enclosed within a packaging material and shaped under reduced pressure to obtain the evaluation model. Here, in the case of the gel (Y1p), the particle size refers to the particle diameter of particles or powder of the water-absorbent crosslinked polymer, the particles or powder being swollen by absorbing a liquid such as water or the colorable aqueous solution (A). The particle size of the gel (Y1p) in this specification is a value obtained by measuring the major axes (portion with the largest particle size) of at least 10 particles in the gel (Y1p) (swollen gel), and calculating the average thereof. Regarding particles whose major axis is about 1 mm or less, the major axes of 50 or more particles in the gel (Yp) are measured, and the average value thereof is obtained. The particle size of the gel (Yp) before liquid absorption is typically about 0.005 to 1.6 mm. In the case of the gel (Y2p), the particle size refers to the particle size of finally obtained particles after crosslinking (particle size measured by the above-described method).

There is no specific limitation on the shape of the gel (Yp), and various shapes may be taken such as spheres, substantial spheres, flakes, irregular shapes (shapes obtained when a lump is crushed), or pellets. In view of operability when packing the gel with a packaging material, it is preferable that the gel is substantially in the shape of spheres.

A food packaging material evaluation model can be obtained according to the shape of a packaging material, for example, by packing (e.g., placing or enclosing) the gel (Yp) with the packaging material. For example, in a case where the packaging material is a container having a predetermined three-dimensional shape, it is possible to obtain a food packaging material evaluation model that is made of the gel (Yp) and has the shape of that container. In a case where the packaging material does not have a predetermined three-dimensional shape (e.g., it is in the form of a bag or the like), it is possible to obtain a food packaging material evaluation model that has a desired shape, by placing the gel (Yp) in the packaging material and then shaping the packaging material that contains the gel (Yp). Although it depends on the particle size, the softness, or the like of the gel (Yp), it is possible to form models that have relatively complex shapes, according to the shape of packaging materials.

There is no specific limitation on the raw material and form of the packaging material used for the food packaging material evaluation model of the present invention. A packaging material made of a transparent resin is preferably used because it makes possible to easily confirm the colored state of the colorable aqueous solution (A). However, opaque materials also can be used. For example, a multilayer structure in which a metal layer made of aluminum or the like is disposed on a single-layer or multilayer structure made of the resin, or a multilayer structure in which a metal oxide layer is evaporated or attached to the single-layer or multilayer structure also can be used.

Examples of the form of the packaging material include: a film; a sheet; a bag made of the film or sheet; and a container such as a cup or a bottle.

As such a packaging material, a single-layer or multilayer resin structure commonly used as packaging materials is used. Preferable examples thereof include: single-layer films made of polyesters, polyamides, polyolefins (e.g., polyethylene) or other resins; multilayer films in which these films are combined; and multilayer films in which any one of these films is combined with a film made of a resin having an excellent gas barrier property (e.g., ethylene-vinyl alcohol copolymer, polyvinylidene chloride, polyamides, etc.). In particular, packaging materials constituted by a multilayer structure that has films made of ethylene-vinyl alcohol copolymer, polyvinylidene chloride, or polyamides as constituents are generally used as packaging materials for the food packaging material evaluation model, that is, packaging materials that are to be tested. Packaging materials constituted by soft films are preferably used because after they are formed into packed bodies, the food shape can be freely formed.

The food packaging material evaluation model of the present invention using the particle gel (Yp) can be formed by various methods. For example, the model is prepared by placing the water-absorbent crosslinked polymer particles or powder as the crosslinked polymer (B), the colorable aqueous solution (A), and optionally the humidity control substance (C) and additives described above in a predetermined packaging material such as a container or bag, and forming the particle gel (Y1p). Alternatively, the model is prepared by causing the water-absorbent crosslinked polymer particles or powder to absorb the colorable aqueous solution (A) and the like to prepare the particle gel (Y1p), and sealing and packing the particle gel (Y1p) in a packaging material. Furthermore, as described above, the model is prepared by preparing a gel from an aqueous solution that contains the crosslinkable polymer, the colorable aqueous solution (A), and optionally the humidity control substance (C) and additives described above, forming the gel into particles, crosslinking the resultant using a crosslinking agent or the like, and then enclosing the obtained particle gel (Y2p) within the packaging material.

When the gel (Yp) or the material forming the gel (Yp) is placed in a container or bag to obtain the food packaging material evaluation model, it is preferable that sealing is performed, preferably after discharging a gas, more preferably after discharging a gas under reduced pressure. After the sealing, the gel is preferably shaped into an appropriate shape by applying an external force.

By performing enclosure under reduced pressure as described above, it is possible to easily retain the shape. Furthermore, even if there is penetration of oxygen when introducing the mixture constituted by constituents of the detection composition into a packaging material in the form of a bag or container, it is possible to minimize the influence of the oxygen. Moreover, it is possible to effectively secure close contact between the detection composition and the packaging material.

Alternatively, before placing the gel (Yp) or before placing the material forming the gel (Yp), inert gas replacement is preferably performed in advance. For example, inert gas replacement may be performed after forming the gel (Yp) from constituents of the detection composition. Alternatively, an inert gas may be blown into the colorable aqueous solution (A), and then a process of forming the gel (Yp) by impregnating the crosslinked polymer (B) with the colorable aqueous solution (A) may be performed also under an inert gas atmosphere. Alternatively, crosslinking may be performed after preparing uncrosslinked gel particles, and performing inert gas replacement. With such inert gas replacement, coloring of the color reagent (A1) with a trace amount of the object substance (X) (e.g., dissolved oxygen gas) contained in constituents of the detection composition is avoided, so that a sensitive test can be performed.

After sealing the detection composition, heat sterilization or ultraviolet sterilization can be performed, if necessary. With this treatment, it is possible to reduce the influence of microorganisms on the detection composition, and to detect what influence appears on the packaging material due to the sterilization treatment per se. In a case where such heat sterilization or ultraviolet sterilization is performed, chemically crosslinked synthetic polymer is preferably used.

In the food packaging material evaluation model using the particle gel (Yp), upon contact between the gel (Yp) and the object substance (X) (e.g., oxygen gas), the object substance (X) is diffused relatively freely between the gel particles. Accordingly, the particle gel (Yp) has an advantage of being capable of obtaining relatively high detection sensitivity compared with the case of the gel (Yb) described below (section 5 below).

(4.2) The Detection Composition and the Food Packaging Material Evaluation Model, Containing the Block (Lump) Gel The block gel (Yb) also may be the block gel (Y1b) constituted by the gel (Y1), or the block gel (Y2b) constituted by the gel (Y2). These block gels can be prepared respectively by the first method and by the method based on the second method for preparing the particle gel.

For example, the block gel is prepared as follows by the first method. First, a water-absorbent crosslinked polymer in the form of blocks is prepared. The colorable aqueous solution (A), and optionally the humidity control substance (C) and additives described above are added to the polymer and absorbed by the polymer to form block gel (Y1b). The ratio between the crosslinked polymer (B) and the colorable aqueous solution (A) in the gel (Y1b) is similar to that in the gel (Y1p).

This method is excellent in that in a case where the food packaging material evaluation model is in a relatively simple shape, the model can be simply and easily prepared.

As the method based on the second method, there is the following method.

First, a mixture is prepared that contains a polymer (crosslinkable polymer) capable of forming the crosslinked polymer (B), the colorable aqueous solution (A), and optionally a crosslinking agent, the humidity control substance (C), and additives described above. This mixture is placed in a bag, container, or the like made of a predetermined packaging material, sealed, shaped into a desired form, and then subjected to crosslinking treatment. When the crosslinking agent is contained, the mixture is allowed to stand without any treatment, or optionally subjected to heating, electron beam irradiation, and thus a crosslinking reaction progresses to form the gel (Y2b) in which constituents (the color reagent (A1), etc.) in the colorable aqueous solution (A) are retained in the matrix of the crosslinked polymer (B). The gel (Y2b) having a desired hardness is formed by adjusting the amount of the crosslinking agent, the heating time, the amount of the electron beam irradiation, or the like. As the packaging material, any material can be used that is similar to the packaging materials described in the section of the detection composition using the particle gel.

This process of obtaining the gel (Y2b) requires effort in that crosslinking has to be performed. However, in a case where a gel is required to have a certain hardness and a rough shape, the gel (Y2b) is preferable. That is to say, it is possible to obtain a gel having a desired shape by charging materials capable of forming the gel in a mold and then crosslinking. Also, it is possible to obtain a gel having a desired relatively complex shape by a method in which gel blocks are formed by crosslinking and carved into a desired shape. If the crosslinking density of the gel (Yb2) is too high, the gel per se hampers diffusion of the object substance (X) to some extent. Thus, in a case where the gel is used to detect the object substance (X), penetration of the object substance (X) stops in the vicinity of the gel surface, so that the sensitivity may be lowered. Therefore, it is necessary to select a gel having an appropriate degree of crosslinking, according to the purpose.

As in the case where the particle gel (Yp) is used, inert gas replacement is preferably performed in advance before the block gel (Yb) is placed in a bag, container, or the like. The gel (Y1b) may be enclosed within a bag, container, or the like under an inert gas atmosphere. Alternatively, in the preparation of the gel (Y2b), an inert gas may be blown into the colorable aqueous solution (A) and the solution containing the crosslinkable polymer, respectively, and then the colorable aqueous solution (A) and the solution containing the crosslinkable polymer may be mixed also under an inert gas atmosphere. With such inert gas replacement, a sensitive test can be performed by avoiding coloring of the color reagent (A1) with a trace amount of the object substance (X) (e.g., dissolved oxygen gas) that is contained in constituents of the detection composition.

In the above-described process, in a case where the gel (Y1b) is placed in a bag or container, or in a case where the mixture capable of forming the gel (Y2b) is placed in a bag or container, a method is recommended in which after these materials are placed, the bag or container is sealed, preferably after discharging a gas, more preferably after discharging a gas under reduced pressure. By performing sealing under reduced pressure, it is possible to easily retain the shape. Furthermore, even if there is penetration of the object substance (X) such as oxygen when placing the materials in the bag or container, it is possible to minimize the influence of the substance. Moreover, it is possible to effectively secure close contact between the detection composition and the packaging material.

After sealing the bag or container, heat sterilization or ultraviolet sterilization can be performed, if necessary. With this treatment, it is possible to reduce the influence of microorganisms on the detection composition, and to detect what influence appears on the packaging material due to the sterilization procedure per se.

In this manner, the detection composition containing the block gel (Yb) is sealed and packed with the packaging material, so that the food packaging material evaluation model having a desired shape is obtained.

In a case where the block gel (Yb) is used, a food model made of only the gel (Yb) also may be shaped, without enclosing the gel within the packaging material. For example, in the first method, a water-absorbent polymer having a desired block shape is prepared, and the colorable aqueous solution (A) are added to the polymer and absorbed by the polymer. Thus, the food model is obtained. In the second method, a mixture containing the colorable aqueous solution (A) and the crosslinkable polymer is placed in a bag or a container having a predetermined shape, crosslinked, and then taken out from the bag or container, to obtain a gel having a predetermined shape. The present invention also encompasses such a food model.

This gel is taken as the food model, without any treatment, or after being cut, if necessary. Such a food model is used, for example, to detect the object substance (X) such as oxygen, by being enclosed as appropriate within the packaging material such as a predetermined bag or container.

There is no specific limitation on the shape of the food packaging material evaluation model and the food model containing the block gel (Yb). In view of shape stability, a substantially integrated product having a predetermined shape is preferable.

(5) Detection of the Object Substance (X) and Evaluation of the Packaging Material, Using the Food Packaging Material Evaluation Model The thus obtained food packaging material evaluation model can be a model for a packed body that is obtained by packing a predetermined food with a predetermined packaging material (e.g., packed body obtained by placing food in a bag or container, and sealing the bag or container). Accordingly, it is possible to detect the object substance (X) penetrating through the packaging material, or a through gap or pinhole of the packaging material, under a predetermined condition. It is also possible to evaluate the performance of the packaging material per se.

Upon contact of the object substance (X) with the colorable aqueous solution (A) in the gel, the color reagent (A1) in the colorable aqueous solution (A) is colored, and thus penetration of the object substance (X) is visually confirmed. Accordingly, in a case where the food packaging material evaluation model is allowed to stand, for example, in air, it is possible to detect the degree of oxygen penetrating through the packaging material, or if there is a defect such as a pinhole in the packaging material, it is possible to detect oxygen penetrating from this point. It is also possible to check penetration of a specific gas such as hydrogen chloride gas, not in air but in a predetermined atmosphere. Furthermore, it is possible to check deterioration of the packaging material when immersed into a predetermined liquid such as hot water.

In order to visually observe coloring, a highly transparent material is preferably selected as the detection composition and the packaging material. However, opaque materials also may be used depending on the purpose. For example, when food is packed with an opaque packaging material, it is possible to observe a defect (e.g., pinhole) of the opaque packaging material.

For example, a bag or the like is prepared in which one face is an opaque film and the other face is a transparent film having a sufficient barrier property, and this bag is used to form the food packaging material evaluation model. If observation is performed through the surface of the transparent film, since the transparency of the detection composition that is a content of the model is high, the colored state of the composition can be observed. Therefore, if there is a defect in the opaque packaging material, the position and degree of the defect can be observed. Alternatively, if the composition is packed using an opaque packaging material, it can be also recommended to provide a window in a part of the packaging material, and cover the window with a transparent material having a high barrier property.

When the object substance (X) penetrates into the packed body, the object substance (X) is diffused in the particle or block gel. In a case where the gel (Y) is in the form of particles, the object substances (X) is diffused directly between adjacent gel particles, or via a liquid that may be exist in a gap between gel particles. As a result, the object substance (X) can be detected with good sensitivity. In the packed body, regardless whether the gel (Y) is in the form of particles or in the form of blocks, the overall shape is retained well, and the colorable aqueous solution (A) can be prevented from freely flowing or convectively circulating. Accordingly, for example, in a case where there is a pinhole defect in a part of the packaging material and the object substance (X) is penetrating only from this point, coloring occurs only in the vicinity of the defect portion, and the colored portion becomes larger over time. Thus, the defect position and the defect degree can be easily detected. In a case where the gel (Y) is in the form of particles, since the object substance (X) is diffused more easily, detection sensitivity and detection speed of the composition are more excellent.

Thus, by using the detection composition or the food packaging material evaluation model of the present invention, it is possible to detect penetration of the object substance (X) into the packed body, or to evaluate the packaging material. For example, when various types of food are packed using various packaging materials such as a film, a sheet, a cup, or a bottle, it is possible to detect the object substance (X) such as oxygen penetrating into the packed body. Moreover, it is possible to accurately judge, for example, whether the object substance (X) is penetrating through the entire container, or penetrating via a cap or sealed portion.

The detection composition or the food packaging material evaluation model of the present invention can be used also to evaluate packed bodies of materials other than food. For example, in a case where a material to be packed is drugs, cosmetics, or general chemicals, it is possible to detect penetration of the object substance (X) into the packed body that contains such a material. Furthermore, it is possible to detect a defect or the like of the packaging material.

EXAMPLES

Hereinafter, examples of the present invention will be described. In the examples, it will be described on a case where the object substance (X) is oxygen, but the present invention is not limited to these examples.

Preparation of the Colorable Aqueous Solution (A)

First, 4.5 mg of methylene blue as the color reagent (A1), 162 mg of reducing agent $SnCl_2.2H_2O$ as the adjustment substance (A2), and 3 ml of 0.2N hydrochloric acid were dissolved in 59 ml of distilled water (distilled water in which dissolved oxygen had been purged with nitrogen for 30 minutes). The mixture was stirred while heating at 85° C. for 30 minutes until the color of the mixture was changed from blue to colorless. Thus, a colorable aqueous solution (A) that was colorless and used for detecting oxygen (hereinafter, may be referred to as a methylene blue solution (1)) was obtained.

Example 1.1

1. Preparation of the Composition for Detecting Oxygen

A crosslinked maleic anhydride-isobutene copolymer resin powder (equivalent to a KI gel 201K (product name) sold by Kuraray Trading Co., Ltd., except for the particle size and the shape; indicated as a KI gel in Tables 1 to 3) was used as the water-absorbent resin. Here, the KI gel used in the examples in this specification is a crosslinked polymer obtained by crosslinking a maleic anhydride/isobutene (1:1) alternating 20 copolymer using polyethyleneimine. Then, 3.1 g of the crosslinked maleic anhydride-isobutene copolymer powder was added to 62 ml of the methylene blue solution (1), and stirred at room temperature for 30 minutes to give a mixture (hereinafter, may be referred to as a detection composition 1). This mixture was mainly constituted by spherical gel 25 particles that had absorbed the methylene blue solution (1), and their average particle size was 2 mm. The average particle size was obtained by placing the mixture in a transparent bag, measuring from the exterior of the bag the diameter (length of the major axis portions) of 10 gel particles that had absorbed the methylene blue solution in the bag, and calculating their average.

2. Food Packaging Material Evaluation Models

The detection composition was placed in each of four types of bags (size 5 cm×7 cm) made of multilayer films having predetermined structures shown in Table 1. The bags were heat-sealed while vacuuming air through an opening portion using a vacuum packaging machine to enclose the detection composition within the bags. After enclosed, the detection composition was shaped by hand into a substantially rectangular solid having a thickness of 5 mm to give food packaging material evaluation models. The raw material and the structure of the multilayer films are shown in Table 1.

3. Detection of Oxygen Penetration State

The food packaging material evaluation models above mentioned were allowed to stand in air at 30° C. and 80% RH (relative humidity), and visually observed over time. Table 1 shows the colored state of an oxygen detection composition 1 in the interior of the packed bodies. During this test, the shape of the food packaging material evaluation models was not substantially changed, and the contents of the packed bodies did not become fluid. In Table 1, CPP refers to cast polypropylene; EVOH refers to an ethylene-vinyl alcohol copolymer; PET refers to polyethylene terephthalate; and PE refers to polyethylene. The same is applied to other tables and other portions in the specification.

TABLE 1

| | | Gel | | Retort/ | The number of days passed | | | |
|---|---|---|---|---|---|---|---|---|
| | | Type of crosslinked polymer | Particle size/ (mm)*[1] | boiling treatment | After 1 day | After 3 days | After 1 week | After 1 month |
| Example 1.1 | Multilayer film 1 | KI gel | 2.0 | none | colorless | colorless | colorless | slightly colored blue |
| | Multilayer film 2 | KI gel | 2.0 | none | colorless | colorless | colorless | slightly colored blue |
| | Multilayer film 3 | KI gel | 2.0 | none | colorless | slightly colored blue | colored blue | colored blue |
| | Multilayer film 4 | KI gel | 2.0 | none | colored blue | colored blue | colored blue | colored blue |

*[1]particle size in gel state of crosslinked polymer particles
Structure of multilayer film
Multilayer film 1: CPP/adhesive layer/EVOH/adhesive layer/CPP
(50 μm/10 μm/20 μm/10 μm/50 μm)
Multilayer film 2: nylon/adhesive layer/EVOH/adhesive layer/CPP
(15 μm/10 μm/20 μm/10 μm/50 μm)
Multilayer film 3: PET/adhesive layer/nylon/adhesive layer/CPP
(10 μm/10 μm/15 μm/10 μm/50 μm)
Multilayer film 4: only PE (commercially available PE bag; product name Unipack A-4 manufactured by Seisannipponsha Ltd.)

Multilayer films similar to the above were prepared, and food packaging material evaluation models were produced in the same manner as described above, except that a nondestructive oxygen meter (using an oxygen meter Fibox 3 manufactured by PreSens) was attached to the inner faces of the films, and distilled water was used instead of the methylene blue solution (1). The models were stored as described above, and the oxygen concentration in the interior of the packed bodies was measured. FIG. 1 shows the relationship between the storage period and the amount of oxygen accumulated in the interior of the packed bodies. The colored state in Table 1 well corresponded to the amount of oxygen accumulated.

Example 1.2

Food packaging material evaluation models were produced using the multilayer films 1 to 3 based on Example 1.1. Next, the models were subjected to boiling sterilization at 85° C. for 30 minutes. Then, the models were allowed to stand in air at 30° C. and 80% RH, and visually observed over time. Table 2 shows the colored state of the detection composition in the interior of the packed bodies.

The oxygen concentration in the interior of the packed bodies was measured using the nondestructive oxygen meter in the same manner as in Example 1.1. The oxygen concentration corresponded to the colored state in the interior of the packed bodies well. Therefore, it is found that impairment of the barrier property caused by the boiling treatment in some types of multilayer films was clearly detected by the colored state.

Example 1.3

Food packaging material evaluation models were produced using the multilayer films 1 to 3 based on Example 1.1. Next, the models were subjected to retort sterilization at 120° C. for 30 minutes. Then, the models were allowed to stand in air at 30° C. and 80% RH, and visually observed over time. The results are shown in Table 3. During this test, even with retort treatment, the shape of the food packaging material evaluation models was not substantially changed, and the contents of the packed bodies did not become fluid.

The oxygen concentration in the interior of the packed bodies was measured using the nondestructive oxygen meter in the same manner as in Example 1.1. The oxygen concen-

TABLE 2

| | | Gel | | Retort/ | The number of days passed | | | | |
|---|---|---|---|---|---|---|---|---|---|
| | | Type of crosslinked polymer | Particle size (mm)*[1] | boiling treatment | Immediately after boiling | After 1 day | After 3 days | After 1 week | After 1 month |
| Example 1.2 | Multilayer film 1 | KI gel | 2.0 | boiling | colorless | colorless | colorless | slightly colored blue | colored blue |
| | Multilayer film 2 | KI gel | 2.0 | boiling | colorless | colorless | colorless | colorless | slightly colored blue |
| | Multilayer film 3 | KI gel | 2.0 | boiling | colored blue | colored blue | colored blue | colored blue | colored blue |

*[1]particle size in gel state of crosslinked polymer particles
Structure of multilayer film
Multilayer film 1: CPP/adhesive layer/EVOH/adhesive layer/CPP
(50 μm/10 μm/20 μm/10 μm/50 μm)
Multilayer film 2: nylon/adhesive layer/EVOH/adhesive layer/CPP
(15 μm/10 μm/20 μm/10 μm/50 μm)
Multilayer film 3: PET/adhesive layer/nylon/adhesive layer/CPP
(10 μm/10 μm/15 μm/10 μm/50 μm)

tration corresponded to the colored state in the interior of the packed bodies well. Thus, a change in the barrier property of the multilayer films caused by the retort treatment could be detected.

solution in the bag by means of a microscope from the exterior of the bag, and calculating their average. In each particle, the longest portion (major axis) of the particle was taken as the diameter.

TABLE 3

| | | Gel | | Retort/ | The number of days passed | | | | |
|---|---|---|---|---|---|---|---|---|---|
| | | Type of crosslinked polymer | Particle size (mm)*1 | boiling treatment | Immediately after retort | After 1 day | After 3 days | After 1 week | After 1 month |
| Example 1.3 | Multilayer film 1 | KI gel | 2.0 | retort | colorless | colorless | slightly colored blue | colored blue | colored blue |
| | Multilayer film 2 | KI gel | 2.0 | retort | colorless | colorless | colorless | slightly colored blue | colored blue |
| | Multilayer film 3 | KI gel | 2.0 | retort | colored blue | colored blue | colored blue | colored blue | colored blue |

*1 particle size in gel state of crosslinked polymer particles
Structure of multilayer film
Multilayer film 1: CPP/adhesive layer/EVOH/adhesive layer/CPP
(50 μm/10 μm/20 μm/10 μm/50 μm)
Multilayer film 2: nylon/adhesive layer/EVOH/adhesive layer/CPP
(15 μm/10 μm/20 μm/10 μm/50 μm)
Multilayer film 3: PET/adhesive layer/nylon/adhesive layer/CPP
(10 μm/10 μm/15 μm/10 μm/50 μm)

Example 2.1

1. Preparation of the Composition for Detecting Oxygen

First, 1.2 g of crosslinked maleic anhydride-isobutene copolymer resin fine powder (product name KI gel-201K-F2, sold by Kuraray Trading Co., Ltd.), which is a water-absorbent resin, was added to 62 ml of the methylene blue solution (1), and stirred at room temperature for 30 minutes to give a mixture (hereinafter, this mixture may be referred to as a detection composition 2). This mixture was mainly constituted by irregularly shaped gel particles that had absorbed the methylene blue solution (1), and their average particle size 2. Production of Food Packaging Material Evaluation Models and Detection of the Oxygen Penetration State By using the mixture (the detection composition 2) and multilayer films with various structures, various food packaging material evaluation models were produced in the same manner as in Example 1.1. The models were allowed to stand in air at 30° C. and 80% RH (relative humidity), and their colored state was observed over time. During this test, the shape of the food packaging material evaluation models was not substantially changed, and the contents of the packed bodies did not become fluid. The test result is shown in Table 4.

TABLE 4

| | | Gel | | Retort/ | The number of days passed | | | |
|---|---|---|---|---|---|---|---|---|
| | | Type of crosslinked polymer | Particle size (mm)*1 | boiling treatment | After 1 day | After 3 days | After 1 week | After 1 month |
| Example 2.1 | Multilayer film 1 | KI gel - 201K-F2 | 0.058 | none | colorless | colorless | colorless | slightly colored blue |
| | Multilayer film 2 | KI gel - 201K-F2 | 0.058 | none | colorless | colorless | colorless | slightly colored blue |
| | Multilayer film 3 | KI gel - 201K-F2 | 0.058 | none | colorless | slightly colored blue | colored blue | colored blue |
| | Multilayer film 4 | KI gel - 201K-F2 | 0.058 | none | colored blue | colored blue | colored blue | colored blue |

*1 particle size in gel state of crosslinked polymer particles
Structure of multilayer film
Multilayer film 1: CPP/adhesive layer/EVOH/adhesive layer/CPP
(50 μm/10 μm/20 μm/10 μm/50 μm)
Multilayer film 2: nylon/adhesive layer/EVOH/adhesive layer/CPP
(15 μm/10 μm/20 μm/10 μm/50 μm)
Multilayer film 3: PET/adhesive layer/nylon/adhesive layer/CPP
(10 μm/10 μm/15 μm/10 μm/50 μm)
Multilayer film 4: only PE
(commercially available PE bag; product name Unipack A-4 manufactured by Seisannipponsha Ltd.)

was 0.058 mm. The water absorption ratio was 52 times its own weight. The average particle size was obtained by placing the mixture in a transparent bag, measuring the diameter of 50 gel particles that had absorbed the methylene blue Multilayer films similar to the above were prepared, and food packaging material evaluation models were produced in the same manner as described above, except that a nondestructive oxygen meter (using an oxygen meter Fibox 3 manufactured by PreSens) was attached to the inner faces of the films, and distilled water was used instead of the methylene blue solution (1). The models were stored as described above, and the oxygen concentration in the interior of the packed bodies was measured. The oxygen concentration in the interior of packed bodies corresponded to the colored state in the interior of the packed bodies well.

Example 2.2

Food packaging material evaluation models were produced using the multilayer films 1 to 3 based on Example 2.1. Next, the models were subjected to boiling sterilization at 85° C. for 30 minutes. Then, the models were allowed to stand in air at 30° C. and 80% RH, and visually observed over time. Table 5 shows the colored state of the detection composition in the interior of the packed bodies.

the barrier property caused by the boiling treatment in some types of multilayer films was clearly detected by the colored state.

Example 2.3

Food packaging material evaluation models were produced using the multilayer films 1 to 3 based on Example 2.1. Next, the models were subjected to retort sterilization at 120° C. for 30 minutes. Then, the models were allowed to stand in air at 30° C. and 80% RH, and visually observed over time. The result is shown in Table 6. During this test, even with retort treatment, the shape of the food packaging material evaluation models was not substantially changed, and the contents of the packed bodies did not become fluid.

The oxygen concentration in the interior of the packed bodies was measured using the nondestructive oxygen meter

TABLE 5

| | | Gel | | Retort/ | The number of days passed | | | | |
|---|---|---|---|---|---|---|---|---|---|
| | | Type of crosslinked polymer | Particle size (mm)*1 | boiling treatment | Immediately after boiling | After 1 day | After 3 days | After 1 week | After 1 month |
| Example 2.2 | Multilayer film 1 | KI gel - 201K-F2 | 0.058 | boiling | colorless | colorless | colorless | slightly colored blue | colored blue |
| | Multilayer film 2 | KI gel - 201K-F2 | 0.058 | boiling | colorless | colorless | colorless | colorless | slightly colored blue |
| | Multilayer film 3 | KI gel - 201K-F2 | 0.058 | boiling | colored blue | colored blue | colored blue | colored blue | colored blue |

*1 particle size in gel state of crosslinked polymer particles
Structure of multilayer film
Multilayer film 1: CPP/adhesive layer/EVOH/adhesive layer/CPP
(50 μm/10 μm/20 μm/10 μm/50 μm)
Multilayer film 2: nylon/adhesive layer/EVOH/adhesive layer/CPP
(15 μm/10 μm/20 μm/10 μm/50 μm)
Multilayer film 3: PET/adhesive layer/nylon/adhesive layer/CPP
(10 μm/10 μm/15 μm/10 μm/50 μm)

The oxygen concentration in the interior of the packed bodies was measured using the nondestructive oxygen meter in the same manner as in Example 2.1. The oxygen concentration corresponded to the colored state in the interior of the packed bodies well. Therefore, it is found that impairment of in the same manner as in Example 2.1. The oxygen concentration corresponded to the colored state in the interior of the packed bodies well. Thus, a change in the barrier property of the multilayer films caused by the retort treatment could be detected.

TABLE 6

| | | Gel | | Retort/ | The number of days passed | | | | |
|---|---|---|---|---|---|---|---|---|---|
| | | Type of crosslinked polymer | Particle size (mm)*1 | boiling treatment | Immediately after retort | After 1 day | After 3 days | After 1 week | After 1 month |
| Example 2.3 | Multilayer film 1 | KI gel - 201K-F2 | 0.058 | retort | colorless | colorless | slightly colored blue | colored blue | colored blue |
| | Multilayer film 2 | KI gel - 201K-F2 | 0.058 | retort | colorless | colorless | colorless | slightly colored blue | colored blue |
| | Multilayer film 3 | KI gel - 201K-F2 | 0.058 | retort | colored blue | colored blue | colored blue | colored blue | colored blue |

*1 particle size in gel state of crosslinked polymer particles
Structure of multilayer film
Multilayer film 1: CPP/adhesive layer/EVOH/adhesive layer/CPP
(50 μm/10 μm/20 μm/10 μm/50 μm)
Multilayer film 2: nylon/adhesive layer/EVOH/adhesive layer/CPP
(15 μm/10 μm/20 μm/10 μm/50 μm)
Multilayer film 3: PET/adhesive layer/nylon/adhesive layer/CPP
(10 μm/10 μm/15 μm/10 μm/50 μm)

Example 3.1

1. Preparation of the Composition for Detecting Oxygen

First, 1.2 g of crosslinked maleic anhydride-isobutene copolymer resin fine powder (product name KI gel-201K, sold by Kuraray Trading Co., Ltd.), which is a water-absorbent resin, was added to 62 ml of the methylene blue solution (1), and stirred at room temperature for 30 minutes to give a mixture (hereinafter, this mixture may be referred to as a detection composition 3). This mixture was mainly constituted by irregularly shaped gel particles that had absorbed the methylene blue solution (1), and their average particle size was 0.24 mm. The average particle size was obtained by placing the mixture in a transparent bag, measuring the diameter of 50 gel particles that had absorbed the methylene blue solution in the bag by means of a microscope from the exterior of the bag, and calculating their average. Wherever measurement was performed in each particle, there was almost no difference in particle size, but the longest portion (major axis) of the particle was taken as the diameter.

2. Production of Food Packaging Material Evaluation Models and Detection of the Oxygen Penetration State By using the mixture (the detection composition 3) and multilayer films with various structures, various food packaging material evaluation models were produced in the same manner as in Example 1.1. As in Example 2.1, the models were allowed to stand in air at 30° C. and 80% RH (relative humidity), and their colored state was observed over time. During this test, the shape of the food packaging material evaluation models was not substantially changed, and the contents of the packed bodies did not become fluid.

In this test, the result was substantially identical to that in Example 2.1.

Example 3.2

Food packaging material evaluation models were produced in the same manner as in Example 3.1. The models were subjected to boiling sterilization at 85° C. for 30 minutes as in Example 2.2. Then, the models were allowed to stand in air at 30° C. and 80% RH, and visually observed over time.

In this test, the result was substantially identical to that in Example 2.2.

Example 3.3

Food packaging material evaluation models were produced in the same manner as in Example 3.1. The models were subjected to retort sterilization at 120° C. for 30 minutes as in Example 2.3. Then, the models were allowed to stand in air at 30° C. and 80% RH, and visually observed over time.

In this test, the result was substantially identical to that in Example 2.3.

Example 4.1

1. Preparation of the Composition for Detecting Oxygen

First, 1.2 g of crosslinked maleic anhydride-isobutene copolymer resin powder (product name KI gel-201K-GI, sold by Kuraray Trading Co., Ltd.), which is a water-absorbent resin, was added to 62 ml of the methylene blue solution (1), and stirred at room temperature for 30 minutes to give a mixture (hereinafter, this mixture may be referred to as a detection composition 4). This mixture was mainly constituted by substantially spherical gel particles that had absorbed the methylene blue solution (1), and their average particle size was 6.8 mm.

2. Production of Food Packaging Material Evaluation Models and Detection of the Oxygen Penetration State By using the mixture (the detection composition 4) and multilayer films with various structures, various food packaging material evaluation models were produced in the same manner as in Example 1.1. As in Example 2.1, the models were allowed to stand in air at 30° C. and 80% RH (relative humidity), and their colored state was observed over time. During this test, the shape of the food packaging material evaluation models was not substantially changed, and the contents of the packed bodies did not become fluid.

In this test, the result was substantially identical to that in Example 2.1.

Example 4.2

Food packaging material evaluation models were produced in the same manner as in Example 4.1. The models were subjected to boiling sterilization at 85° C. for 30 minutes as in Example 2.2. Then, the models were allowed to stand in air at 30° C. and 80% RH, and visually observed over time.

In this test, the result was substantially identical to that in Example 2.2.

Example 4.3

Food packaging material evaluation models were produced in the same manner as in Example 4.1. The models were subjected to retort sterilization at 120° C. for 30 minutes as in Example 2.3. Then, the models were allowed to stand in air at 30° C. and 80% RH, and visually observed over time.

In this test, the result was substantially identical to that in Example 2.3.

Example 5.1

1. Preparation of the Composition for Detecting Oxygen

First, 0.6 g of crosslinked maleic anhydride-isobutene copolymer resin fine powder (product name KI gel-201K-F2, sold by Kuraray Trading Co., Ltd.) and 0.6 g of crosslinked maleic anhydride-isobutene copolymer resin powder (product name KI gel-201K-G1, sold by Kuraray Trading Co., Ltd.), which are water-absorbent resins, were added to 62 ml of the methylene blue solution (1), and stirred at room temperature for 30 minutes to give a mixture (hereinafter, this mixture may be referred to as a detection composition 5).

2. Production of Food Packaging Material Evaluation Models and Detection of the Oxygen Penetration State By using the mixture (the detection composition 5) and multilayer films with various structures, various food packaging material evaluation models were produced in the same manner as in Example 1.1. As in Example 2.1, the models were allowed to stand in air at 30° C. and 80% RH (relative humidity), and their colored state was observed over time. During this test, the shape of the food packaging material evaluation models was not substantially changed, and the contents of the packed bodies did not become fluid.

In this test, the result was substantially identical to that in Example 2.1.

Example 5.2

Food packaging material evaluation models were produced in the same manner as in Example 5.1 The models were subjected to boiling sterilization at 85° C. for 30 minutes as in Example 2.2. Then, the models were allowed to stand in air at 30° C. and 80% RH, and visually observed over time.

In this test, the result was substantially identical to that in Example 2.2.

Example 5.3

Food packaging material evaluation models were produced in the same manner as in Example 5.1. The models were subjected to retort sterilization at 120° C. for 30 minutes as in Example 2.3. Then, the models were allowed to stand in air at 30° C. and 80% RH, and visually observed over time.

In this test, the result was substantially identical to that in Example 2.3.

Comparative Example 1.1

1. Preparation of the Composition for Detecting Oxygen

First, 200 ml of distilled water (distilled water in which dissolved oxygen had been purged with nitrogen) was added to 4 g of commercially available agar powder (manufactured by Wako Pure Chemical Industries, Ltd.), and heated and stirred at 80° C. for 30 minutes to give an agar solution. Then, 62 ml of the methylene blue solution (1) was added to the agar solution, and heated and stirred at 80° C. for 30 minutes until the color of the solution was changed from blue to colorless. Thus, a colorless agar aqueous solution for detecting oxygen was obtained.

2. Detection of the Oxygen Penetration State

As in Example 1.1, the agar aqueous solution for detecting oxygen was enclosed within each of four types of bags made of multilayer films having predetermined structures. The agar aqueous solution was gelled, and thus packed bodies containing the agar gel for detecting oxygen were obtained. As in Example 1.1, the packed bodies were allowed to stand at 30° C. and 80% RH, and visually observed over time. The result is shown in Table 7. The colored state of the contents was substantially identical to that in Example 1.1. During this test, the shape of the contents of the bags was not substantially changed, but flowability was exhibited to the extent that when the bag was moved, this solution was slightly moved in the bag in which the solution was contained together with the gel.

ation models were subjected to boiling sterilization at 85° C. for 30 minutes. As a result, the contents of the packed bodies were decomposed due to heat, and flowed as a solution. Thus, it was impossible to retain the shape.

After the boiling sterilization, the models were allowed to stand in air at 30° C. and 80% RH, and visually observed over time. Coloring due to a change over time was similar to that in Comparative Example 1.1, but the coloring speed was slightly accelerated compared with the case of Comparative Example 1.1. The reason for this may be that the boiling sterilization lowered the barrier property of the multilayer films.

Comparative Example 1.3

As in Comparative Example 1.1, an agar aqueous solution for detecting oxygen was prepared, and enclosed within bags made of multilayer films to give food packaging material evaluation models. Then, the food packaging material evaluation models were subjected to retort sterilization at 120° C. for 30 minutes. As a result, the contents of the packed bodies were decomposed due to heat, and flowed as a solution. Thus, it was impossible to retain the shape.

After the retort sterilization, the models were allowed to stand in air at 30° C. and 80% RH, and visually observed over time. Coloring due to a change over time was similar to that in Comparative Example 1.1, but the coloring speed was slightly accelerated compared with the case of Comparative Example 1.1. The reason for this may be that the retort sterilization lowered the barrier property of the multilayer films.

Comparative Example 2

First, 4.5 mg of methylene blue, 3 ml of 0.2N hydrochloric acid, and 162 mg of $SnCl_2.2H_2O$ were dissolved in 59 ml of distilled water (distilled water in which dissolved oxygen had been purged with nitrogen), and heated and stirred at 85° C. for 30 minutes until the color of the solution was changed from blue to colorless, to prepare a colorable aqueous solution that was colorless and used for detecting oxygen.

TABLE 7

| | | Gel | | Retort/boiling | The number of days passed | | | |
|---|---|---|---|---|---|---|---|---|
| | | Type | Shape | treatment | After 1 day | After 3 days | After 1 week | After 1 month |
| Comparative Example 1.1 | Multilayer film 1 | agar gel | block | none | colorless | colorless | colorless | slightly colored blue |
| | Multilayer film 2 | agar gel | block | none | colorless | colorless | colorless | slightly colored blue |
| | Multilayer film 3 | agar gel | block | none | colorless | slightly colored blue | colored blue | colored blue |
| | Multilayer film 4 | agar gel | block | none | colored blue | colored blue | colored blue | colored blue |

Structure of multilayer film
Multilayer film 1: CPP/adhesive layer/EVOH/adhesive layer/CPP
(50 μm/10 μm/20 μm/10 μm/50 μm)
Multilayer film 2: nylon/adhesive layer/EVOH/adhesive layer/CPP
(15 μm/10 μm/20 μm/10 μm/50 μm)
Multilayer film 3: PET/adhesive layer/nylon/adhesive layer/CPP
(10 μm/10 μm/15 μm/10 μm/50 μm)
Multilayer film 4: PE (commercially available PE bag; product name Unipack A-4 manufactured by Seisannipponsha Ltd.)

Comparative Example 1.2

As in Comparative Example 1.1, an agar aqueous solution for detecting oxygen was prepared, and enclosed within bags made of multilayer films to give food packaging material evaluation models. Then, the food packaging material evalu- As in Example 1.1, the colorable aqueous solution for detecting oxygen was enclosed within bags made of multilayer films to give packed bodies containing the colorable aqueous solution for detecting oxygen.

As in Comparative Example 1.1, the packed bodies were allowed to stand at 30° C. and 80% RH, and visually observed over time. The colored state of the colorable aqueous solution for detecting oxygen was similar to that in Comparative Example 1.1. However, since the contents of the bags had flowability, they could not be shaped into a predetermined shape.

Example 6

Detection of Defects in Packaging Materials

A bag was produced by thermocompression bonding using a multilayer film 3 having the layer structure (i) shown below for one face of the bag and a multilayer film 2 having the layer structure (ii) for the other face.

(i) CPP layer/adhesive layer/nylon layer/adhesive layer/aluminum layer, from the inner side (50 μm/10 μm/15 μm/10 μm/50 μm)

(ii) CPP layer/adhesive layer/nylon layer/adhesive layer/NCCF multilayer structure, from the inner side (50 μm/10 μm/15 μm/10 μm/about 15 μm)

Figure 2:
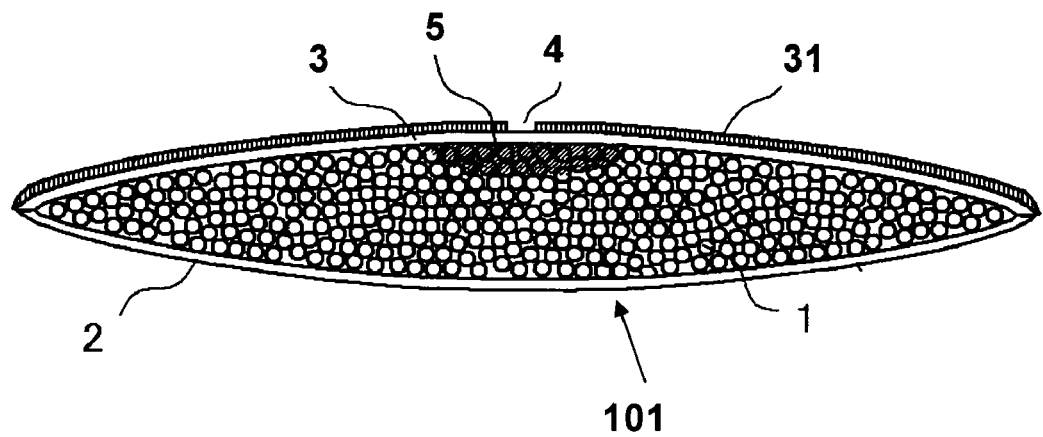
FIG. 2 is a schematic cross-sectional view showing an example of a color state due to penetration of oxygen through a pinhole in a packaging material, in a food packaging material evaluation model of the present invention.

As shown in FIG. 2, this bag is arranged and configured such that one face is made of the multilayer film 2, the other face is made of the multilayer film 3, and the outermost layer of the multilayer film 3 is an aluminum layer 31. A mixture (the detection composition 1; indicated as 1 in FIG. 2) prepared in the same manner as in Example 1.1 was placed in this bag, and the bag was sealed as in Example 1.1 to give a packed body (a food packaging material evaluation model 101).

The NCCF multilayer structure of the above multilayer film 2 is a multilayer structure that is similar to the layered product B-11 in Example 1 of International Publication WO2005/053954, and is a transparent multilayer structure having a high gas barrier property. As the aluminum layer 31 of the multilayer film 3, an aluminum foil in which a hole 4 having a diameter of 0.1 mm was formed with a pin in advance in the center portion was used for a model having a defect in the packaging material.

The thus obtained packed body was allowed to stand at 30° C. and 80% RH (relative humidity), and visually observed over time. As a result, as shown in FIG. 2, a blue colored portion 5 substantially in the shape of a circle that was centered about the hole 4 was observed from the surface of the transparent multilayer film 2 of the packed body. Thus, it was easy to visually confirm from which portion oxygen had penetrated. During this test, the shape of the food packaging material evaluation model was not changed, and its content did not exhibit flowability.

Separately from this, after the obtained packed body was subjected to boiling treatment at 85° C. for 30 minutes or to retort treatment at 120° C. for 30 minutes, the packed body was allowed to stand under the same conditions (at 30° C. and 80% RH), and visually observed over time. In either case, a blue colored portion 5 substantially in the shape of a circle that was centered about the hole 4 was observed from the surface of the transparent multilayer film 2 of the packed body. Thus, it was easy to visually confirm from which potion oxygen had penetrated. During this test, the shape of the food packaging material evaluation model was not changed, and its content did not exhibit flow ability.

Example 7

A bag was prepared in the same manner as in Example 6, and a mixture (the detection composition 2) prepared in the same manner as in Example 2.1 was placed in this bag to give a packed body (food packaging material evaluation model). Using the obtained packed body, a test was conducted as in Example 6.

In this case, the result was similar to that in Example 6. However, in a case where the gel particles were moved when the packed body was handled, and the overall shape was slightly changed, the boundary of the blue colored portion was not clear in some cases.

Example 8

A bag was prepared in the same manner as in Example 6, and a mixture (the detection composition 3) prepared in the same manner as in Example 3.1 was placed in this bag to give a packed body (food packaging material evaluation model). Using the obtained packed body, a test was conducted as in Example 6.

In this case, the result was similar to that in Example 6. However, in a case where the gel particles were moved when the packed body was handled, and the overall shape of the packed body was slightly changed, the boundary of the blue colored portion was not clear in some cases.

Example 9

A bag was prepared in the same manner as in Example 6, and a mixture (the detection composition 4) prepared in the same manner as in Example 4.1 was placed in this bag to give a packed body (food packaging material evaluation model). Using the obtained packed body, a test was conducted as in Example 6. In this case, the result was similar to that in Example 6.

Example 10

A bag was prepared in the same manner as in Example 6, and a mixture (the detection composition 5) prepared in the same manner as in Example 5.1 was placed in this bag to give a packed body (food packaging material evaluation model). Using the obtained packed body, a test was conducted as in Example 6. In this case, the result was similar to that in Example 6.

Comparative Example 3

An agar aqueous solution for detecting oxygen was prepared in the same manner as in Comparative Example 1.1, and then enclosed within a bag in which one face was made of a multilayer film containing an aluminum layer that had a pinhole as in Example 6. The agar aqueous solution was gelled, and thus a packed body (food packaging material evaluation model) containing a block agar gel was obtained. As in Example 6, the packed body was allowed to stand at 30° C. and 80% RH, and visually observed over time. However, when the bag was merely lifted for observation, the agar gel was moved together with the aqueous solution in the interior, and thus the blue colored portion was moved. Therefore, it was impossible to visually confirm clearly from which portion oxygen had penetrated.

Furthermore, a packed body containing a block agar gel was prepared as described above, and then subjected to boiling treatment at 85° C. for 30 minutes or to retort treatment at 120° C. for 30 minutes. As a result, at the end of the boiling sterilization or retort sterilization, the shape of the packed body was not retained. Subsequently, as the packed body was allowed to stand, not only the hole portion, but also the entire content of the bag was colored blue. Therefore, it was impossible to visually confirm from which portion oxygen had penetrated.

Comparative Example 4

First, 4.5 mg of methylene blue, 3 ml of 0.2N hydrochloric acid, and 162 mg of $SnCl_2.2H_2O$ were dissolved in 59 ml of distilled water (distilled water in which dissolved oxygen had been purged with nitrogen), and heated and stirred at 85° C. for 30 minutes until the color of the solution was changed from blue to colorless, to prepare a colorable aqueous solution that was colorless and used for detecting oxygen.

The colorable aqueous solution for detecting oxygen was enclosed within a bag in which one face was made of a multilayer film containing an aluminum layer that had a pinhole as in Example 6, and then allowed to stand at 30° C. and 80% RH. In this case, not only a portion in the vicinity of the hole, but also the entire content was colored blue. Therefore, it was impossible to visually confirm from which portion oxygen had penetrated.

Example 11.1

The detection composition of Example 1.1 was placed in a bag (size 5 cm×7 cm) made of the multilayer film 3 shown in Table 1. The bag was squeezed by hand to remove air in the interior. Then, the bag was heat-sealed to enclose the detection composition within the bag. After enclosed, the detection composition was shaped by hand into a substantially rectangular solid having a thickness of 5 mm to give a food packaging material evaluation model.

The food packaging material evaluation model was allowed to stand in air at 30° C. and 80% RH (relative humidity), and visually observed over time. The result was substantially identical to that in the case of the bag made of the multilayer film 3 in Example 1.1 (see Table 1). However, since unremoved air partially remained between gel particles, coloring was observed also in this portion. During this test, the shape of the food packaging material evaluation model was not substantially changed, and the content of the packed body did not become fluid.

Examples 11.2 to 11.5

Tests were conducted in the same manner as in Example 11.1, except that the detection compositions of Examples 2.1, 3.1, 4.1, and 5.1 were used respectively instead of the detection composition of Example 1.1. As a result, in all Examples, the results were substantially identical to that in the case of the bag made of the multilayer film 3 in Example 1.1 (see Table 1). However, since unremoved air partially remained between gel particles in the case of Example 11.4 (using the composition of Example 4.1), coloring was observed also in this portion.

In all Examples, during this test, the shape of the food packaging material evaluation models was not substantially changed, and the contents of the packed bodies did not become fluid.

Example 12.1

1. Preparation of the Polyvinyl Alcohol Aqueous Solution

A polyvinyl alcohol (hereinafter PVA) aqueous solution was prepared as described below. First, 108 g of PVA (PVA-HC manufactured by Kuraray Co., Ltd.; degree of saponification 99%, degree of polymerization 1700) powder was immersed into 710 ml of water, and heated and stirred at 95° C. for 1.5 hours. Then, the temperature of the obtained solution was lowered to 40° C., and a mixture of 36.7 ml of water and 39.6 g of isopropanol was added thereto. The resultant was stirred for 10 minutes to give a PVA aqueous solution. This solution was taken as a PVA aqueous solution (1).

2. Preparation of the Food Packaging Material Evaluation Model

Then, 15 ml of the methylene blue solution (1) was added to 90 g of the PVA aqueous solution (1), and stirred at room temperature for 30 minutes. As the crosslinking agent, a 10% diluted aqueous solution (titanium lactate concentration 4.5%) of a commercially available 45% titanium lactate solution (TC-300 manufactured by Matsumoto Fine Chemical Co., Ltd.) was prepared. The diluted solution was added to the PVA aqueous solution containing the methylene blue solution (1) to give a colorless mixture. This mixture was immediately placed in a bag (5 cm×7 cm, made of the multilayer film 1) having a multilayer structure, and the bag was heat-sealed while vacuuming air through an W opening portion using a vacuum packaging machine (the structure of the multilayer film 1 is shown in Table 8). Then, the content was shaped by hand into a substantially rectangular solid having a thickness of 5 mm, to give a food packaging material evaluation model (oxygen detection composition enclosed within the bag and shaped).

3. Detection of the Oxygen Penetration State

The food packaging material evaluation model was allowed to stand in air at 30° C. and 80% RH, and visually observed over time. Table 8 shows the colored state of the oxygen detection composition (taken as a detection composition 6) in the interior of the packed body. During this test, the shape of the food packaging material evaluation model was not substantially changed, and the content of the packed body did not become fluid.

A multilayer film similar to the above was prepared, and a food packaging material evaluation model was produced in the same manner as described above, except that a nondestructive oxygen meter (using an oxygen meter Fibox 3 manufactured by PreSens) was attached to the inner face of the film, and distilled water was used instead of the methylene blue solution (1). The model was stored as described above, and the oxygen concentration in the interior of the packed body was measured. The colored state shown in Table 8 corresponded to the oxygen concentration well.

Example 12.2

A food packaging material evaluation model was prepared in the same manner as in Example 12.1, and subjected to boiling sterilization at 85° C. for 30 minutes. Then, the model was allowed to stand in air at 30° C. and 80% RH, and visually observed over time. The colored state of the detection composition is shown in Table 8. During this test, the shape of the food packaging material evaluation model was not substantially changed, and no flowability was exhibited. The oxygen concentration was measured using the nondestructive oxygen meter as in Example 12.1. The colored state shown in Table 8 corresponded to the oxygen concentration well.

Example 12.3

A food packaging material evaluation model was prepared in the same manner as in Example 12.1, and subjected to retort sterilization at 120° C. for 30 minutes. Then, the model was allowed to stand in air at 30° C. and 80% RH, and visually observed over time. The result is shown in Table 8. The oxygen detection composition inside the bag was colored over time. During this test, the shape of the food packaging material evaluation model was not substantially changed, and no flowability was exhibited. The oxygen concentration was measured using the nondestructive oxygen meter as in Example 12.1. The colored state shown in Table 8 corresponded to the oxygen concentration well.

allowed to stand in air at 30° C. and 80% RH, and visually observed over time. The colored state was similar to that in Example 12.3. During this test, the shape of the food pack-

TABLE 8

| | Gel | Multilayer film | Treatment | The number of days passed | | | | |
| --- | --- | --- | --- | --- | --- | --- | --- | --- |
| | | | | Immediately after treatment | After 1 day | After 3 days | After 1 week | After 1 month |
| Example 12.1 | Crosslinked PVA (lump) | Multilayer film 1 | none | — | colorless | colorless | colorless | slightly colored blue |
| Example 12.2 | Crosslinked PVA (lump) | Multilayer film 1 | boiling treatment | colorless | colorless | colorless | slightly colored blue | slightly colored blue |
| Example 12.3 | Crosslinked PVA (lump) | Multilayer film 1 | retort treatment | colorless | colorless | slightly colored blue | slightly colored blue | slightly colored blue |

Structure of multilayer structure
Multilayer film 1: CPP/adhesive layer/EVOH/adhesive layer/CPP
(50 μm/10 μm/20 μm/10 μm/50 μm)

Example 13.1

1. Preparation of the Polyvinyl Alcohol Aqueous Solution

A polyvinyl alcohol (hereinafter PVA) aqueous solution was prepared as described below. First, 180 g of PVA (PVA-105H manufactured by Kuraray Co., Ltd.; degree of saponification 99%, degree of polymerization 500) powder was immersed into 650 ml of water, and heated and stirred at 95° C. for 1.5 hours. Then, the temperature of the solution was lowered to 40° C., and a mixture of 24.5 ml of water and 36.0 g of isopropanol was added thereto. The resultant was stirred for 10 minutes to give a PVA aqueous solution. This solution was taken as a PVA aqueous solution (2).

2. Preparation of the Food Packaging Material Evaluation Model

A food packaging material evaluation model was produced in the same manner as in Example 12.1, using the PVA aqueous solution (2) instead of the PVA aqueous solution (1).

3. Detection of the Oxygen Penetration State

The food packaging material evaluation model was allowed to stand in air at 30° C. and 80% RH as in Example 12.1, and visually observed over time. The oxygen detection composition inside the bag was colored over time, and the colored state was similar to that in Example 12.1. During this test, the shape of the food packaging material evaluation model was not substantially changed, and no flowability was exhibited.

Example 13.2

A food packaging material evaluation model was prepared in the same manner as in Example 13.1, and the obtained food packaging material evaluation model was subjected to boiling sterilization at 85° C. for 30 minutes. Then, the model was allowed to stand in air at 30° C. and 80% RH, and visually observed over time. The colored state was similar to that in Example 12.2. During this test, the shape of the food packaging material evaluation model was not substantially changed, and no flowability was exhibited.

Example 13.3

A food packaging material evaluation model was prepared in the same manner as in Example 13.1, and the obtained food packaging material evaluation model was subjected to retort sterilization at 120° C. for 30 minutes. Then, the model was aging material evaluation model was not substantially changed, and no flowability was exhibited.

Example 14.1

1. Preparation of the Polyvinyl Alcohol Aqueous Solution

A polyvinyl alcohol (hereinafter PVA) aqueous solution was prepared as described below. First, 135 g of PVA (HR-1000 manufactured by Kuraray Co., Ltd. (AQ3010; degree of saponification 99%, degree of polymerization 1000)) powder was immersed into 690 ml of water, and heated and stirred at 95° C. for 1.5 hours. Then, the temperature of the solution was lowered to 40° C., and a mixture of 29.6 ml of water and 38.3 g of isopropanol was added thereto. The resultant was stirred for 10 minutes to prepare a PVA aqueous solution. This solution was taken as a PVA aqueous solution (3).

2. Preparation of the Food Packaging Material Evaluation Model

A food packaging material evaluation model was produced in the same manner as in Example 12.1, using the PVA aqueous solution (3) instead of the PVA aqueous solution (1).

3. Detection of the Oxygen Penetration State

The food packaging material evaluation model was allowed to stand in air at 30° C. and 80% RH as in Example 12.1, and visually observed over time. The oxygen detection composition inside the bag was colored over time, and the colored state was similar to that in Example 12.1. During this test, the shape of the food packaging material evaluation model was not substantially changed, and no flowability was exhibited.

Example 14.2

A food packaging material evaluation model was prepared in the same manner as in Example 14.1, and the obtained food packaging material evaluation model was subjected to boiling sterilization at 85° C. for 30 minutes as in Example 12.2. Then, the model was allowed to stand in air at 30° C. and 80% RH, and visually observed over time. The colored state was similar to that in Example 12.2. During this test, the shape of the food packaging material evaluation model was not substantially changed, and no flowability was exhibited.

Example 14.3

A food packaging material evaluation model was prepared in the same manner as in Example 14.1, and the obtained food packaging material evaluation model was subjected to retort sterilization at 120° C. for 30 minutes as in Example 12.3. Then, the model was allowed to stand in air at 30° C. and 80% RH, and visually observed over time. The colored state was similar to that in Example 12.3. During this test, the shape of the food packaging material evaluation model was not substantially changed, and no flowability was exhibited.

Example 15

Detection of Defects in Packaging Materials

A bag having a structure similar to that in Example 6 was produced. In this bag, one face is made of the multilayer film 3 having the layer structure (i) shown below, and the other face is made of the multilayer film 2 having the layer structure (ii).

(i) CPP layer/adhesive layer/nylon layer/adhesive layer/aluminum layer, from the inner side
(50 μm/10 μm/15 μm/10 μm/50 μm)

(ii) CPP layer/adhesive layer/nylon layer/adhesive layer/NCCF multilayer structure, from the inner side
(50 μm/10 μm/15 μm/10 μm/about 15 μm)

Figure 3:
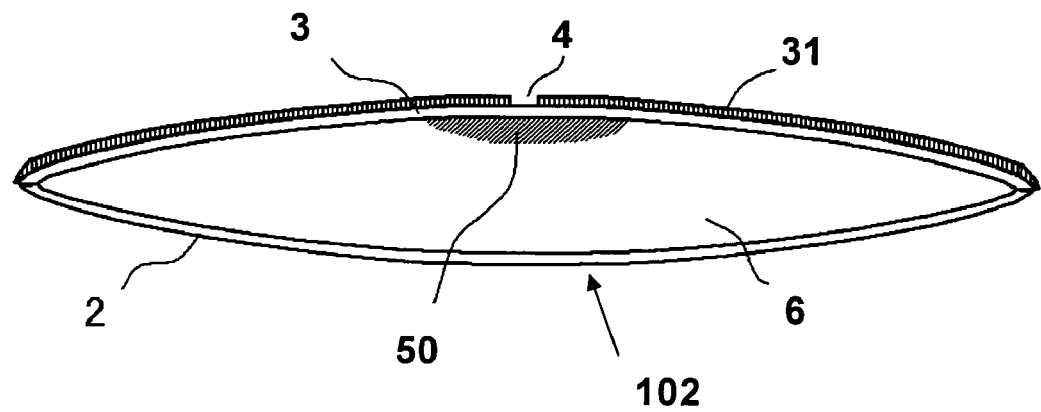
FIG. 3 is a schematic cross-sectional view showing an example of a color state due to penetration of oxygen through a pinhole in a packaging material, in another food packaging material evaluation model of the present invention.

As shown in FIG. 3, this bag is arranged and configured such that one face is made of the multilayer film 2, the other face is made of the multilayer film 3, and the outermost layer of the multilayer film 3 is the aluminum layer 31. A mixture (the detection composition 6; indicated as 6 in FIG. 3) containing the PVA aqueous solution (1), a methylene blue solution, and a crosslinking agent, which were similar to those used in Example 12.1, was placed in this bag, and the bag was sealed to give a packed body (a food packaging material evaluation model 102).

As the aluminum layer 31 of the multilayer film 3, an aluminum foil in which a hole 4 having a diameter of 0.1 mm was formed with a pin in advance in the center portion was used for a model having a defect in the packaging material.

The thus obtained packed body was allowed to stand at 30° C. and 80% RH (relative humidity), and visually observed over time.

Separately from this, after the obtained packed body was subjected to boiling treatment at 85° C. for 30 minutes or to retort treatment at 120° C. for 30 minutes, the packed body was allowed to stand under the same conditions (at 30° C. and 80% RH), and visually observed over time. In either case, as shown in FIG. 3, a blue colored portion 50 substantially in the shape of a circle that was centered about the hole 4 was observed from the side of the transparent multilayer film 2 of the packed body. Thus, it was easy to visually confirm from which portion oxygen had penetrated. In either condition, during this test, the shape of the food packaging material evaluation model was not changed, and its content did not exhibit flowability.

Example 16

A food packaging material evaluation model was prepared in the same manner as in Example 15, using a mixture containing the PVA aqueous solution (2) as obtained in Example 13.1, a methylene blue solution, and a crosslinking agent, and the obtained model was evaluated. In this case, the result was substantially identical to that in Example 15.

Example 17

A food packaging material evaluation model was prepared in the same manner as in Example 15, using a mixture containing the PVA aqueous solution (3) as obtained in Example 14.1, a methylene blue solution, and a crosslinking agent, and the obtained model was evaluated. In this case, the result was substantially identical to that in Example 15.

Industrial Applicability

With the detection composition of the present invention, a predetermined object substance (X) such as oxygen can be effectively detected. In a case where this composition is placed in a container, bag, or the like made of a predetermined packaging material, and a packed body is formed by sealing the container, bag, or the like, a food packaging material evaluation model is obtained with which penetration of the object substance (X) can be effectively detected, and the packaging material can be evaluated. When this food packaging material evaluation model is used, penetration of the object substance (X) can be detected under common storage conditions, and under conditions for treating packed food, e.g., sterilization conditions, and the performance of the packaging material can be preferably evaluated.

The invention claimed is:

1. A composition
comprising a gel (Y)
wherein
the gel (Y) comprises a colorable aqueous solution (A) that changes color upon contact with oxygen,
and a water-absorbent crosslinked polymer (B), wherein the colorable aqueous solution (A) is retained in the water-absorbent crosslinked polymer (B) to form the gel (Y), and
wherein the water-absorbent crosslinked polymer (B) is a crosslinked product of a maleic anhydride-isobutene copolymer or its salt.

2. The composition of claim 1, wherein the gel (Y) is obtained by a process comprising crosslinking a mixture that comprises the colorable aqueous solution (A) and a crosslinkable polymer.

3. The composition of claim 1, wherein the gel (Y) is in the form of particles.

4. The composition of claim 3, wherein the particles have a particle size of 0.01 to 10 mm.

5. The composition of claim 1, wherein the gel (Y) is a substantially integrated product having a predetermined shape.

6. The composition of claim 1, wherein when the gel (Y) is heated at 85° C. for 15 minutes in the presence of water in an amount of 100 parts by weight or more with respect to 100 parts by weight of the water-absorbent crosslinked polymer (B), the shape of the gel (Y) can be retained.

7. The composition of claim 1, wherein the colorable aqueous solution (A) is an aqueous solution that comprises a color reagent (A1) colored upon contact with oxygen, and an adjustment substance (A2), and the adjustment substance (A2) can keep the color reagent (A1) colorless until contact with oxygen.

8. The composition of claim 7, wherein the color reagent (A1) is methylene blue.

9. The composition of claim 7, wherein the adjustment substance (A2) is stannous chloride, and the composition further comprises a hydrochloric acid.

10. The composition of claim 7, further comprising a humidity control substance (C) for adjusting equilibrium vapor pressure.

11. A food packaging material comprising the composition of claim 1.

12. A food packaging material obtained by a process comprising sealing and packing the composition of claim 1, with a packaging material.

13. A food packaging material obtained by a process comprising performing inert gas replacement on the composition of claim 1, placing the composition in a packaging material in the form of a container or bag, and then sealing the packaging material.

14. A food packaging material obtained by a process comprising placing the composition of claim 1 in a packaging material in the form of a container or bag, discharging a gas, and then sealing the composition with the packaging material.

15. A food packaging material obtained by a process comprising placing the composition of claim 1 in a packaging material in the form of a container or bag, sealing the composition with the packaging material, and then performing ultraviolet sterilization or heat sterilization.

16. A method for detecting penetration of oxygen into a packed body, comprising:
    sealing and packing the composition of claim 1 with a packaging material to obtain a packed body,
    bringing an obtained packed body into contact with a gas or liquid that comprises oxygen and
    detecting oxygen based on coloring of the composition in the interior of the packed body, thereby detecting penetration of oxygen into the packed body.

17. A method for evaluating a packaging material, comprising:
    sealing and packing the composition of claim 1 with a packaging material to obtain a packed body;
    bringing an obtained packed body into contact with a gas or liquid that comprises oxygen and
    detecting oxygen that has penetrated into the packed body based on coloring of the composition in the interior of the packed body, thereby evaluating the packaging material.

18. The method of claim 17, wherein the packaging material is a food packaging material.

19. The composition of claim 7, wherein the color reagent (A1) is methylene blue, methyl red, anthocyanin, anthraquinone, β-carotene, methyl orange, litmus, bromothymol blue, or phenolphthalein.

20. A method of detecting the presence of oxygen comprising exposing the composition of claim 1 to a body which may comprise oxygen.

* * * * *